United States Patent [19]

Seiderman

[11] 4,034,750
[45] July 12, 1977

[54] ELECTROCHEMICALLY LINKING COLLAGEN FIBRILS TO ANIMAL TISSUE

[76] Inventor: Maurice Seiderman, 3306 Deronda Drive, Hollywood, Calif. 90068

[21] Appl. No.: 570,384

[22] Filed: Apr. 22, 1975

[51] Int. Cl.² .......................................... A61F 13/00
[52] U.S. Cl. ............................. 128/155; 128/334 R; 128/DIG. 8
[58] Field of Search ............... 128/82.1, 155–157, 128/268, 172.1, DIG. 8, 334 R; 3/1

[56] References Cited
U.S. PATENT DOCUMENTS 2,202,566   5/1940   Schulte ............................. 128/156
3,563,228   2/1971   Seiderman ....................... 128/334 R
3,742,955   7/1973   Battista et al. .................. 128/DIG. 8
3,810,473   5/1974   Cruz et al. ...................... 128/DIG. 8

Primary Examiner—Lawrence W. Trapp
Attorney, Agent, or Firm—Bacon & Thomas

[57] ABSTRACT

Skin-like collagen membranes are adapted for protecting a wound, lesion or the like on animal bodies. These collagen membranes are semipermeable and are electrochemically-linked to the damaged collagen fibrils of the animal body. This electrochemical biological junction is established iontophoretically from an electric potential derived from the body's own inherent electrical characteristics or a galvanic couple.

25 Claims, 5 Drawing Figures

ELECTROCHEMICALLY LINKING COLLAGEN FIBRILS TO ANIMAL TISSUE

BACKGROUND OF THE INVENTION

1. Field of the Invention

The present invention relates to the covering of a wound, lesion or the like on an animal body with an adherent, skin-like collagen membrane to effect protection therefor during the healing process. The invention also relates to an iontophoretic process whereby collagen fibrils are electrochemically-linked with each other and to the wound or lesion site to provide such membranes.

2. Description of the Prior Art

The need to provide protection for a wound, lesion or the like on an animal body during the healing thereof has long been recognized. This need is predicated upon many factors, not the least of which are the requisites of precluding infectious or other foreign material from entering the open wound as well as the desirability of alleviating pain and loss of body fluids attendant such open areas on the body.

Various techniques have been devised in the past to achieve some amount of protection for open wounds, burns, etc. by means of bandaging or application of some physical barrier intimate the open wound. However, mere physical barriers have proved inadequate in many respects, the most notable deficiency including the inability of these bandage-like protective coatings to retain fluids while permitting oxygen permeability therethrough. Accordingly, the ability to curtail drainage of bodily fluids which accumulate in the wound as well as the ability to maintain oxygen permeability are foreclosed. In an effort to obviate these deficiencies, various surgical grafting techniques have been developed.

Probably the most widely accepted and employed of these grafting procedures involves the application of skin to the area of interest. Fundamentally, these skin graftings are capable of providing enhanced permeability due to their inherent characteristics and thus minimize the masking effects of such physical barriers as bandages. As a norm, the skin employed for such grafts may be provided by a donor or may be removed from the patient to be treated himself. It has been shown, however, that the use of donated skin provides concomitant problems of, particularly, rejection. Such rejection, which results from the introduction of material foreign to the recipient's body, manifests a lack of adherence and accompanying sloughing off of grafted area. Accordingly, to avert this rejection phenomena, the most successful grafting may be achieved by employing skin sections removed from the patient to be treated. However, under many circumstances this is also highly undesirable.

In an effort to provide a viable alternative to skin grafting to effect protection for open wounds, lesions and the like on an animal body, investigation into the adherence of other naturally occurring materials to the area of interest has witnessed wide-spread attention. It has been determined that collagen may admirably be employed to achieve these ends. Collagen is a proteinaceous fiber existing as a fundamental constituent of connective tissue, cartilage and bone in all mammalians. Collagen possesses numerous inherent characteristics which render it readily adaptable for use as a protective film or membrane for a wound, etc., such characteristics comprising, inter alia, flexibility, substantial insolubility in water and body fluids, permeability to these fluids as well as permeability to oxygen and many commonly used topical antibiotics. Another characteristic of collagen rendering it highly suitable for such application is its ability to electrochemically-link between and among fibrils to effect a membranous film.

In recognition of the highly favorable, inherent characteristics of collagen which render it adaptable for providing protective films for wounds, lesions and the like, I have developed a process for the formation of adherent films disclosed in my U.S. Pat. No. 3,563,228 issued Feb. 16, 1971, incorporated herein by reference. Briefly described, that earlier patent relates to the application of an electric field, of suitable polarity, to a dispersion of undenatured collagen fibrils to cause electrochemical-linking between the fibrils of the dispersion. The collagen, thus applied, is also capable of linking to native collagen fibrils exposed at the wound site to effect a highly adherent, protective surface thereover.

The essence of the ability of collagen to form such protective surfaces rests in large part with the physical and chemical characteristics of the fibrils in the dispersion. The preparation of collagen fibrils to form such a dispersion, which may subsequently be used to form electrochemically-linked collagen membranes, involves a process of cutting, chopping, beating and otherwise damaging some portion of the fibrils, thus though to expose polar sites. The number of polar sites exposed along the length of the fibril will vary depending upon preparatory treatment, with some fibrils having polar sites uncovered entirely along the length thereof. The fibrils in the dispersion do not have the opportunity to contact and join each other by mating polarities. However, the statistical distribution yields sufficient opposing polarities located sufficiently close to each other that an additional electrical impetus electrochemically-links the fibrils together. Once linked, the collagen membrane exhibits substantial physical strength and is no longer soluble in the fluid of the initial dispersion.

Microscopic examination reveals a substantial degree of both mechanical interlocking and joining between the fibrils of the collagen membrane and those exposed at the wound site. Accordingly, such films are extremely adherent to a wound and provide a great degree of protection therefor. As such films are semipermeable to bodily fluids, no undue accumulation thereof is exhibited. Similarly, as the membranes are oxygen permeable, prompt healing of the wound is enhanced.

In recognizing the advance over the prior art provided by my U.S. Pat. No. 3,563,228, it would be desirable to provide these adherent, skin-like protective coatings but without the need for application of an external power source to provide the iontophoretic impetus therefor, it being appreciated that the electric apparatus are often bulky and, ofttimes, require the patient to be treated at some central location. Accordingly, it is desirable to be able to provide these protective coatings by continuous treatment of the patient without significant restrictions upon ambulation or the necessity of confinement.

SUMMARY OF THE INVENTION

As an improvement over my prior patent cited supra, I propose to effect the electrochemical-linking of the collagen fibrils applied proximate a wound, lesion or the like on an animal body by iontophoretic action, but without the necessity of an external, bulky, expensive apparatus. It is, therefore, the major object of this invention to effect the creation of an electrochemically-linked collagen coating exhibiting a tenacity approaching that of skin in a simple, yet efficient manner.

It is yet another object of this invention to employ the inherent electrical potential of the animal body to be treated to provide the necessary iontophoretic impetus for the electrochemical-linking of collagen applied proximate a wound, lesion or the like on the animal body to effect such an adherent, skin-like protective coating.

It is still another object of this invention to effect the electrochemical-linking of collagen fibrils to form an adherent, skin-like protective, biological junction over a wound, lesion, burn or the like on an animal body, with the iontophoretic impetus thererfor derived from a galvanic couple integrally contained on a bandage substrate or surgical dressing.

It is still a further object of this invention to provide such a bandage or dressing with a functionally effective amount of either a topical or systemic medicament or other bio-affecting active agent, e.g., an antibacterial agent.

These and other objects of this invention will become obvious to those skilled in the art from an inspection of the following detailed description and appended claims when viewed in conjunction with the figures of drawings.

In accordance with the present invention, it has now been determined that a collagen suspension or dispersion may be prepared, which suspension is desirably isotonic in character and optionally possesses selected metallic salts corresponding to those found in the animal body and present in similar minute proportions to provide an electrolyte for the conduction of an electrical current. In one embodiment of the invention, when such a collagen suspension is disposed proximate a wound, lesion or the like on the animal body to be treated, an electric field will be established between the suspension and the underlying area of tissue which exhibits a net effective negative electrical characteristic.

Optionally, should it be desired to effect such a protective coating more rapidly than is possible by employing only the inherent electrical characteristics of the body to be treated, an auxiliary power source may be supplied. In accordance with this embodiment, such an auxiliary power supply is incorporated integrally with a bandage or dressing substrate bearing the collagen to be electrochemically-linked. This power source comprises a galvanic couple which employs, inter alia, natural body fluids as an electrolyte. The galvanic interaction between electrodes will create an electric field which provides the iontophoretic impetus for electrochemically-linking of the applied collagen to yield an adherent, skin-like protective layer thereof over the tissue area to be treated.

DETAILED DESCRIPTION OF THE INVENTION

Figure 1:
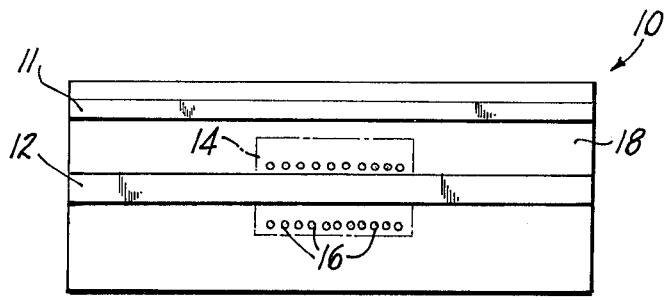
FIG. 1 is a top elevation view of a bandage according to one embodiment of the present invention.

The invention will now be described in detail with respect to various embodiments, it being understood that each embodiment is predicated upon the ability to iontophoretically cause the electrochemical-linking of collagen fibrils with adjoining fibrils and the available damaged fibrils of the animal to be treated.

As regards this phenomenon, it is well understood that any particle exhibiting a charge imbalance, whether such imbalance results from ionic or polar characteristics of the particle, will preferentially align and migrate when subjected to the influence of an electric field. In view of the fact that collagen fibrils are dipolar in nature and posses discrete charged sites along the length thereof, these fibrils will be influenced by an applied electric field. Accordingly, should collagen fibrils be applied proximate a wound, lesion or the like on an animal body, these applied collagen particles may be caused to electrochemically-link with each other and with damaged collagen of the tissue area to be treated, to thus form an adherent, skin-like layer effected by the electrochemical-linking of said applied and native collagen fibrils.

As used in the context of the present invention, the term bandage is meant to include all varieties of surgical dressings, regardless of physical configuration, which may be applied over a wound site to effect treatment therefore. Thus, the present invention envisions utility extending from the rather small adhesive bandages to large dressings of several square feet which may be applied to burn victims.

The first embodiment to be described makes use of the inherent, negative electrical potential of an animal body to provide the necessary iontophoretic impetus for electrochemical-linking of collagen fibers contained in a dispersion applied proximate the area to be treated. To achieve these ends, a collagen dispersion is prepared in the same manner as that described in U.S. Pat. No. 3,563,228 save for the fact that the collagen concentration in the instant dispersion is greater than the preferred 0.25% to 1% by weight concentration recited therein, e.g., up to about 50% by weight concentration, but most desirably having the consistency of soft table butter. More specifically, the instant collagen suspension may be prepared from bovine deep flexor tendon which has been cleaned and trimmed of fat and other extraneous matter, frozen, and subsequently sliced perpendicular to the longitudinal axis of the tendeons to a suitable length of about 0.001 mm to 0.5 mm, preferably from 0.2 mm to 0.5 mm, albeit such a length is not critical. The collagen fibrils may then be disaggregated by treatment with proteolytic enzyme such as commercial ficin. This treatment may be achieved, for example, by gentle aggitation for approximately 1 hour at 35° F. in an aqueous solution of ficin. These fibrils are then washed with distilled water and treated with aqueous sodium chloride solution of approximately 1% concentration for about 1 hour in two or three successive treatments. Having thus been prepared, these fibrils are added to a mixture of equal parts of ethanol and water, optionally containing approximately 0.2% cyanoacetic acid if long-term storage is anticipated; this mixture is then aggitated at a temperature approaching the freezing point thereof and subsequently homogenized by a conventional homogenizer. Optionally, the collagen dispersion may be produced according to the teachings of either U.S. Pat. No. 3,368,911 or the process of Battista as described in the Journal of Applied Polymer Science, 11, 41–498 (1967).

Such a dispersion of, for example, 10% collagen concentration, will exhibit a paste-like consistency similar to that of soft butter. This paste is then enhanced for better conductivity by additions of saline (usually in amounts ranging from between 0.1% to 1.0% by weight), such as sodium chloride or potassium chloride, preferably in amounts to render the paste isotonic; that is, 0.9%. Metallic salts corresponding to those indigenous to the animal body may also be added in similar minute quantities, e.g., in amounts ranging between about 0.01% and 10% by weight. Selection of these salts, specifically to be rich in positive ions, is well within the purview of the skilled artisan.

This paste may then be applied locally over the area to be treated. An electrical field will be established between the collagen paste dispersion and the animal body; the paste will exhibit an overall positive charge while the areas surrounding the wound site will exhibit an effective negative electrical potential. However, the relative electrical potential thus established is relatively slight and, thus, the desired electrochemical-linking of the collagen fibrils proceeds rather slowly. Accordingly, it may be desirable to provide an auxiliary power source, operating in conjunction with the body's inherent electrical characteristics, to enhance this action.

Figure 2:
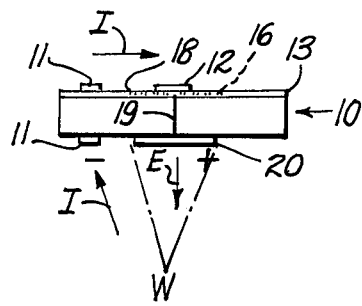
FIG. 2 is a side elevation view of the bandage of FIG. 1.
Figure 3:
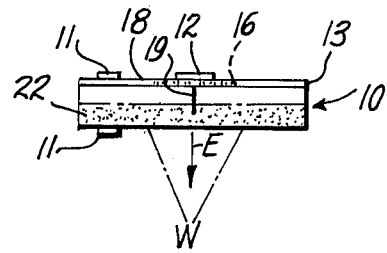
FIG. 3 is a side elevation view, similar to that of FIG. 2, showing an alternate embodiment of the present invention.

FIGS. 1-3 illustrate another embodiment of the present invention wherein a galvanic couple is employed to achieve the necessary electrical impetus for electrochemical-linking. FIG. 1 illustrates a bandage, generally designated as 10, bearing electrodes 11 and 12. The bandage may be selected from numerous commercial varieties well known to those skilled in the art and is necessary only to provide a suitable substrate upon which the galvanic electrodes may be deposited, as well as a suitable quantity of collagen. Preferably, the bandage will be comprised of a liquid impervious top layer 13, as shown in FIGS. 2 and 3, possessing an area 14 wherein a plurality of perforations 16 are located. Characteristics such as flexibility, absorbency, etc. will be dictated by individual cases and are well known to the skilled artisan.

Electrodes 11 and 12, which form the galvanic couple, may be fabricated from strips of suitable electrochemical material, such as metal. The electrodes may be adhered to the upper surface of the bandage in any desired manner, such as adhesive paste. Optionally, these electordes may be fabricated by dispersing the desired electrochemically-active material in a volatile carrier to form an ink or paint which may then be applied to the bandage. A quantity of dry electrolyte 18 is disposed intermediate electrodes 11 and 12.

As viewed in FIG. 2, a collagen coating, such as that fully described hereinabove, designated as 20 is applied to the opposite side of the bandage and dried. Electrode 12 is caused to be maintained in electrical contact with the collagen coating by internally disposed conductive member 19, although electrode 12 may be overwrapped about the end of the bandage thereby providing this desired electrical contact. Electrode 11 is caused to be electrically insulated from both electrode 12 and the collagen coating 20 and is overwrapped about the bandage 10 or otherwise caused to make electrical contact with the skin of the animal to be treated at a location apart from the wound area, W.

It is necessary that electrode 12 exhibits a positive standard reduction potential with respect to electrode 11 to effect the proper polarity therebetween; that is, current should flow from electrode 12, throuh the coated collagen layer to the tissue area of interest, and thence to electrode 11, through electrolyte 18 and back to electrode 2 to complete the electrical circuit, as depicted in FIG. 2. Thus, if the positive strip 12 is made of a metal which may be strongly attacked by electrolysis, it may enter the wound, lesion, etc. Accordingly, while the electrode 12 may be fabricated from any harmless metal such as aluminum, it is preferred that this positive electrode be made from carbon. As regards the composition of electrode 11, any metallic material meeting the foregoing standard reduction potential criterion and one which further exhibits a harmless effect on the body may be suitably employed.

The bandage according to this embodiment may be activated by applying a few drops of water to the perforated area 14 which will wet both the electrolyte 18 and the dried collagen dispersion coating 20. Optionally, the body's own fluids, such as blood or serum, may be employed to these ends. Once this has been achieved, galvanic action between the two electrodes will assist the inherent negative potential of the animal body by providing a current of proper polarity and attendant electric field to augment that naturally existing. Accordingly, collagen the hydrated coating will electrochemically-link according to the lines of electric force, E, and the fibrils will form a film or membrane linked with damaged fibrils of the wound to effect an adherent, skin-like protective coating.

An alternate embodiment of the topic bandage is depicted in FIG. 3 wherein there is now incorporated a discrete region 22 which is porous in nature. In this embodiment, the material from which the bandage is fabricated is such that the collagen dispersion described supra may be impregnated therein; for example, foamed polyurethane. Otherwise, this bandage will operate identical to the description for the bandage described in FIGS. 1 and 2.

Further, it will be obvious to the skilled artisan that the bandage depicted in FIGS. 1-3, and described above, need not employ the saline or metallic salt components in the collagen dispersion during initial processing thereof. The action of the galvanically generated electric field will, in some cases, be sufficient to supplant the requirement of these constituents by using the body's own fluid components.

Figure 4:
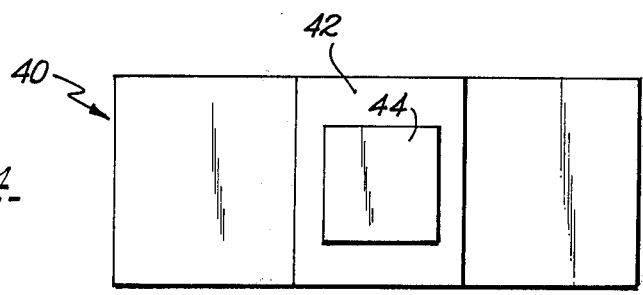
FIG. 4 is a bottom elevation view of a bandage according to yet another embodiment of the present invention.
Figure 5:
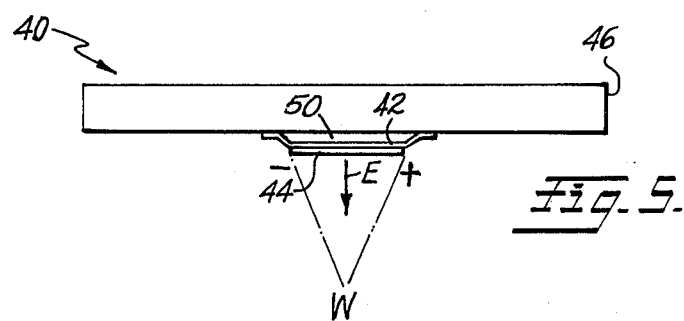
FIG. 5 is a side elevation view of the bandage of FIG. 4.

Another, and the most preferred embodiment in accordance with the present invention is illustrated in FIGS. 4 and 5. In FIG. 4 there is shown a bandage generally designated as 40 bearing an area 42 which is a film of electrochemically active material, to be described more fully hereinbelow. Borne upon the film 42 is a film of collagen 44.

In the embodiment depicted in FIGS. 4 and 5, the electrical potential is derived from a single active electrode, 42, which is in contact with the skin of the patient to be treated proximate the wound area. The electrode 42 is chosen to ensure it possesses negative electrical characteristics with respect to the collagen film, as shown in FIG. 5. Accordingly, the functional electrical characteristics of the bandage shown in FIGS. 4 and 5 are similar to those described above.

The material's selection for electrode 42 is restricted primarily upon considerations such as standard reduction potential to ensure the electrode maintains a negative potential with respect to the collagen film; the propensity for dissolution, to minimize the introduction of the electrode material within the wound area, as well as other considerations well known to the skilled artisan. Preferred electrode materials are, for example, aluminum, mild silver protein and zinc. However, when zinc is employed, due to its galvanic activity, it is preferable to form electrode 42 as a narrow strip adjacent collagen film 44, in contradistinction to the film shown in FIG. 4 wherein the electrode is adjacent the entire periphery of collagen film 44.

Particularly beneficial results may be realized upon employing a mild silver protein film for electrode 42. Mild silver protein, a colloidal solution prepared by the interaction of protein and silver oxide and containing about 19 to 23% silver, is a well known bacteriostatic agent. Only a small fraction of the silver is in a ionizable state and, thus, mild silver protein is not irritating but, in fact, is somewhat demulcent. For a more comprehensive understanding of the uses and effects of mild silver protein, see Goodman and Gillman, *The Pharmacological Basis of Theraputics*, 3rd Edition, McMillan, 1969.

The mild silver protein membrane may be fabricated to exhibit either a propensity to disintegrate in moisture or, with good wet strength to preclude such occurrence. Accordingly, the electrode material itself may take an active role in the healing process.

Another of the preferred electrode materials is aluminum, a relatively innocuous material with little tendency to dissolve when the bandage is employed. A bandage similar to that depicted in FIG. 5 was fabricated for purposes of experimentation. The bandage 40 has an upper, liquid impervious layer 46 and conveniently possesses a pressure sensitive adhesive (not shown) on the obverse side in order to facilitate adherence of the bandage to the area for treatment. This test employed a conventional bandage commercially marketed under the trademark CURAD. A thin foil of aluminum, for example, 0.002 to 0.003 inches thick, was adhered over a gauze area 50 of the bandage. A paste of collagen was prepared in accordance with the process described above and deposited over the electrode 42 by means of a doctor blade. The collagen membrane, 44, may be either supported or unsupported, and may be processed to yield the collagen dispersible or insoluble in water, as desired. Once the bandage was assembled as shown in FIG. 5, a drop of salin solution was placed upon the collagen film. Potentiometric tests were performed upon the bandage at that time and indicated a voltage of 0.5 volts between the electrode and collagen film, and a current of 400 microamperes.

Other bandages were fabricated in similar fashion employing electrode materials as set forth in Table 1. The voltage and current developed by each of these bandages is likewise set forth in Table 1.

TABLE 1

| Electrode Material | Voltage (v) | Current ($\mu a$) |
| --- | --- | --- |
| Aluminum | 0.5 | 400 |
| Zinc | 1.2 | 200 |
| Tin | 0.5 | 50 |
| Titanium | 0.15 | 25 |
| Tantalum | 0.1* | 2.5 |

*reverse polarity

As is readily apparent from the foregoing description, a bandage made in accordance with the present invention enjoys a broad range of utility and may beneficially be employed in the treatment of any wound, lesion and the like. It has been observed that the collagen dispersion borne upon the bandage substrate electrochemically-links in a very short amount of time under the influence of the electrical potential derived from the galvanic source. Moreover, the collagen film adherently and tenaciously attaches to the wound site through both mechanical and chemical linkages with the exposed, damaged collagen fibrils of the wound. Accordingly, it has further been observed that the bandage substrate itself may be removed in a relatively short amount of time, leaving behind this highly adherent, skin-like collagen film. Moreover, it has been observed that the collagen film thus applied to the wound site, upon limited dehydration, will contract somewhat and tend to close the wound in a natural manner. These, and other benefits, are realized upon application of materials totally acceptable to the animal undergoing treatment and, accordingly, rejection is rare.

Moreover, various modifications may be made to the bandage and/or collagen dispersion of the present invention. For example, mild silver protein may be mixed with the collagen dispersion to form a paste of enhanced electrochemical activity. Further, the conductivity of mild silver protein has been found to be enhanced by a fine spray or mist of ammonia prior to use. Thus, the relative electrical potential between electrodes and/or the collagen film is capable of a wide range of selection in order that the bandage be adapted for tailor-make operation. This is particularly true as the electrochemical-linking phenomenon is a strong function of electrical potential and may be advanced or retarded based upon materials selection.

Yet further modifications to the bandage have been determined both feasible and desirable. For example, various drug entities or active agents, especially those amphoteric in nature, may be compounded with the collagen dispersion in functionally effective quantities, as is the case with mild silver protein. These medicaments include antibacterials, antibiotics and the like, such as tetracycline and streptomycin and also chondroitin-sulfate, which medicaments further enhance regeneration of damaged tissue and aid the joining of collagen tissue. Tests to determine the efficacy of additions of these medicaments reveal an intensification of the healing process and a two-fold reduction in the required time of treatment. Further, these medicaments may be either topical or systemic.

It has also been determined that the notable benefits of practicing the present invention may be realized by impregnating simple tissue paper with the appropriate collagen dispersion, with or without additions, rather than depositing the collagen upon a conventional bandage substrate. The impregnated paper, whether readily disintegratable or possessing wet strength, may then be utilized for treatment, optionally in combination with any of the galvanic sources described above. In like vein, the collagen dispersion, with or without additions, may be dried to a film, supported or unsupported, and used without need of any substrate. These embodiments may prove highly beneficial for treatment of extensive wound areas such as, for example, burns.

Also, the collagen film may be electrically linked prior to its application to the wound area. A preferred process to form this pre-linked film is disclosed in my copending abandoned application Ser. No. 444,001, filed Feb. 20, 1974 for "Preparation of Collagen Films and Articles and Use Thereof", incorporated herein by reference and relied upon. Thus, the pre-linked film or membrane may be placed over the area to be treated and one of the foregoing galvanic sources applied to effect linking between the collagen membrane and damaged collagen fibrils of the wound.

It will be understood that various omissions and substitutions and changes in the form and details of the bandage and collagen dispersion may be made by those skilled in the art without departing from the spirit of the invention. It is the intention, therefore, to be limited only as indicated by the scope of the following claims.

What is claimed is:

1. A collagen dispersion adapted for topical application to an animal body with a wound, lesion or the like, and useful for providing an adherent skin-like protective membrane of electrochemically-linked collagen fibrils over said wound, lesion or the like, said collagen fibrils also capable of electrochemiclly-linking with exposed collagen fibrils of the wound, lesion or the like to form an electrochemical biological junction, said dispersion having a paste-like consistency and including collagen fibrils and an electrochemically effective amount of an electrolyte.

2. The collagen dispersion of claim 1, wherein said electrolyte is selected from the group comprising sodium chloride, potassium chloride, and mixtures thereof.

3. The bandage of claim 2 further comprising a quantity of silver protein medicament borne on said substrate.

4. The collagen dispersion of claim 1, wherein said collagen fibrils are from 0.001 to 0.5 mm in length.

5. The collagen dispersion of claim 1, wherein said electrolyte component is present in the concentration of from 0.1% to 1.0% by weight.

6. The collagen dispersion of claim 1, further comprising a metallic salt component present in the concentration of from 0.01% to 10.0% by weight.

7. A bandage adapted for topical application to an animal body with a wound, lesion or the like, and useful for providing an adherent, skin-like protective membrane of electrochemically-linked collagen fibrils over said wound, lesion or the like, said bandage comprising a substrate bearing a quantity of dried collagen dispersion defined by claim 1.

8. The bandage of claim 7 further comprising first and second electrodes intimately adhered to said substrate.

9. The bandage of claim 8, wherein said first electrode is characterized as possessing a positive standard reduction potential with respect to said second electrode, said first electrode further characterized as being in operative electrical contact with said collagen dispersion.

10. The bandage of claim 8 further comprising a dry electrolyte disposed intermediate said first and second electrodes.

11. The bandage of claim 7, wherein said collagen dispersion is coated on said substrate.

12. The bandage of claim 7, wherein said collagen dispersion is impregnated into said substrate.

13. The bandage of claim 8, wherein said first and second electrodes are fabricated from strips of electrochemically active materials and adhered to said substrate by an adhesive.

14. The bandage of claim 8, wherein said first and second electrodes are each comprised of electrochemically active materials having been applied to said substrate as a dispersion thereof with a volatile carrier.

15. The bandage of claim 7 further comprising a quantity of silver protein medicament borne on said substrate.

16. A bandage adapted for topical application to an animal body with a wound, lesion or the like thereon and useful for providing an adherent, skin-like protective membrane of electrochemically-linked collagen fibrils over said wound, lesion or the like, comprising:
  a. A film-forming quantity of collagen fibrils; and
  b. a film of an electrochemically active material upon which said fibrils are borne in electrically cooperative relationship, wherein said collagen is capable of application to said wound, lesion or the like, and upon introduction of fluid to said bandage, said electrochemically active material is capable of generating a galvanic current, whereby said collagen fibrils electrochemically-link to form said adherent, skin-like protective membrane.

17. The bandage of claim 16 further comprising a functionally-effective amount of mild silver protein mixed with said collagen fibrils.

18. The bandage of claim 16, wherein said electrochemically active material is selected from the group comprising aluminum, zinc, titanium, tin and mild silver protein.

19. The bandage of claim 16, wherein said electrochemically active material is aluminum.

20. The bandage of claim 16, wherein said electrochemically active material is mild silver protein.

21. The bandage of claim 16, wherein said callagen fibrils are undenatured.

22. A method for treating a wound, lesion or the like on an animal body comprising the steps of applying to said body area a film-forming quantity of a dispersion of collagen fibrils in cooperation with an electrochemically active material, and at least partially hydrolyzing said dispersion by introducing an electrolyte, whereby said electrochemically active material produces a galvanic current through said dispersion to thereby form an electrochemically-linked biological junction of collagen fibrils, characterized as an adherent, skin-like protective membrane over said wound, lesion or the like, and said membrane further characterized as being electrochemically-linked to available, damaged collagen fibrils of said wound, lesion or the like.

23. The method of claim 22, wherein said collagen dispersion and said electrochemically active material are borne upon a bandage substrate, said method further comprising the step of removing said bandage substrate after said electrochemically-linked biological junction has formed.

24. The bandage of claim 16, further comprising a medicament.

25. The bandage of claim 24, wherein said medicament is amphoteric.

* * * * *